United States Patent [19]

Kopf

[11] 4,235,701
[45] Nov. 25, 1980

[54] AROMATICS FROM DRIPOLENE

[75] Inventor: Fred W. Kopf, Ocean City, N.J.

[73] Assignee: Atlantic Richfield Company, Los Angeles, Calif.

[21] Appl. No.: 25,628

[22] Filed: Mar. 30, 1979

[51] Int. Cl.$^3$ .................... C10G 45/32; C07C 15/04
[52] U.S. Cl. ..................................... 208/57; 208/96; 208/144; 585/434
[58] Field of Search .............. 260/673.5, 668 D; 585/413, 419, 434; 208/57, 60, 95–96, 139, 141, 143–144

[56] References Cited

U.S. PATENT DOCUMENTS

| | | | |
|---|---|---|---|
| 2,953,612 | 9/1960 | Haxton et al. | 208/57 X |
| 2,976,336 | 3/1961 | Housam et al. | 585/412 |
| 3,261,877 | 7/1966 | Dierschke et al. | 585/413 |
| 3,316,316 | 4/1967 | Johnston | 208/57 X |
| 3,470,085 | 9/1969 | Parker | 208/57 X |
| 3,472,909 | 10/1969 | Raymond | 208/57 X |
| 3,496,095 | 2/1970 | Lewis | 208/57 X |
| 3,625,879 | 12/1971 | Horne et al. | 208/57 |
| 3,806,553 | 4/1974 | Kovach et al. | 585/251 |
| 3,992,465 | 11/1976 | Juguin et al. | 208/96 X |

*Primary Examiner*—Delbert E. Gantz
*Assistant Examiner*—G. E. Schmitkons
*Attorney, Agent, or Firm*—John R. Ewbank

[57] ABSTRACT

In an olefin plant in which ethylene, propylene and butenes are prepared, a dripolene fraction is recovered, hydrogenated and a $C_6$–$C_7$ hydrogenated hydrocarbon stream derived from such hydrogenated dripolene is aromatized in the presence of a hydrogen rich recycle stream and in the presence of a catalyst containing platinum and chloride on aluminum whereby the aromatics content is increased above the approximately 64% aromatics content of the hydrogenated $C_6$–$C_7$ hydrocarbon stream. The aromatics are extracted from the liquid effluent from the aromatization zone.

2 Claims, No Drawings

AROMATICS FROM DRIPOLENE

FIELD OF INVENTION

This invention relates to the preparation of a mixture of benzene and toluene by the hydrogenative aromatizing of a hydrocarbon stream derived from dripolene.

PRIOR ART

When hydrocarbons are subjected to cracking in the presence of steam to produce a mixture comprising ethylene, propylene, butadiene, isoprene, piperylene, cyclopentadiene and related materials, there are also produced certain $C_{6+}$ hydrocarbons which have created problems for the petrochemical industry. The term "dripolene" has been applied to the liquid fraction derived as a by-product from the steam cracking of hydrocarbons. Such product has also sometimes been called pyrolysis gasoline. Although dripolene contains a significant proportion of benzene and toluene, it has been a difficult material to utilize because of the propensity of some of the components to undergo polymerization, gum formation and/or other reactions when exposed to air, and/or light and/or heat soaking. During the steps of recovering components such as butadiene and/or isoprene, the commercial composition of dripolene can undergo significant changes by reason of the propensity of cyclopentadiene and/or derivative of cyclopentadiene to undergo dimerization and/or polymerization. The chemical composition of a dripolene stream can be affected by the feed stock to the steam cracking step and by the processing prior to the withdrawal of the dripolene stream from the process.

In a recently constructed plant for the production of olefins, the effluent from the steam cracking zone was subjected to a series of steps for the recovery of a stream of ethylene, a stream of propylene, a butadiene stream and a crude isoprene stream leaving a residue of liquid comprising significant amounts of $C_5$ hydrocarbons (pentenes, and piperylene and cyclopentadiene), benzene, toluene and other hydrocarbons. By distillation of such dripolene, a $C_5$–$C_7$ stream was withdrawn and treated as a pyrolysis naphtha and/or dripolene. Such dripolene was initially hydrogenated in the presence of a palladium on alumina catalyst to saturate the diolefins and thereafter subjected to more severe hydrogenation over a cobalt molybdate catalyst to provide a hydrogenated pyrolysis gasoline. Such hydrogenated pyrolysis gasoline was subjected to solvent extraction to provide a stream of benzene and a stream of toluene and a stream of raffinate, which raffinate was directed to the gasoline pool. Such plant was operated for several years so that millions of gallons of raffinate were thus directed to the gasoline plant operations by reason of the difficulties of dealing with products derived from dripolene. Moreover, the solvent extraction step was relatively costly by reason of the presence of compounds such as methyl cyclopentane and methyl cyclohexane in such hydrogenated pyrolysis gasoline. Various alternative processing proposals were considered and found unacceptable by reason of the history of the difficulties connected with processing streams derived from dripolene.

Horne et al U.S. Pat. No. 3,625,879 subjects a depentenized dripolene to severe hydrogenation, followed by reforming, followed by very severe hydrodealkylation and hydrocracking followed by mild hydrogenation followed by distillation to recover a technical grade of benzene without extractive distillation. All xylene, toluene, mesitylene, etc. are hydrodealkylated to benzene and all paraffins are cracked into components having boiling points remote from that of benzene by reason of the severity of said hydrodealkylation step.

Kovach et al U.S. Pat. No. 3,806,553 employs a rhenium sulfide catalyst to hydrogenate the diolefin and olefin content of a $C_6$–$C_7$ heart cut containing more than 50% of a mixture of benzene and toluene, said heart cut being derived from dripolene. Either hydrocracking or reforming of the hydrogenated dripolene, or both, provides a stream from which benzene and toluene can be distilled without solvent extraction Other patents disclose various treatments of dripolene comprising multiple stages of hydrogenative treatment for increasing the already high benzene content, but as regards the present invention, each such patent and the aggregation of such literature, fail to teach the subject matter as a whole of the present invention. Notwithstanding the teachings of Horne et al, Kovach et al, and/or other dripolene literature, the process engineers designing the recovery of benzene from dripolene designed a process in which the hydrogenated $C_6$–$C_7$ dripolene was solvent extracted to provide smaller quantities of benzene and toluene than provided by the present invention. The long standing demand for an attractive economical process for obtaining attractive yields of benzene from dripolene has long remained unsatisfied.

SUMMARY OF INVENTION

In accordance with the present invention, a dripolene stream formed as a by-product from the manufacture of olefins is subjected to hydrogenation to provide a saturated hydrocarbon stream which is subjected to severe hydrogenative aromatization over a catalyst comprising an alumina carrier, an aluminum halide acidic component and a platinum hydrogenation component. The product from the hydrogenative aromatizing treatment includes some normally gaseous hydrocarbon but the liquid recovery is high. The liquid recovered from the hydrogenative aromatizing step is subjected to aromatics extraction and distillation to prepare streams of toluene, benzene, and raffinate. Because such feedstock to the extraction has a low concentration of naphthenes and is highly paraffinic the cost of aromatics extraction per gallon of benzene is attractively low.

The invention is further clarified by reference to a plurality of illustrative embodiments.

CONTROL A

Kerosene is steam cracked to provide gaseous olefins comprising ethylene, propylene, butenes, and butadiene. A by-product liquid is recovered. Isoprene is recovered from the pyrolysis naphtha. Other $C_5$ hydrocarbons as well as $C_{8+}$ hydrocarbons are removed in preparing a $C_6$ $C_7$ heartcut dripolene containing significant amounts of benzene and toluene. Such heartcut is subjected to two stages of hydrogenation, first over a palladium on alumina catalyst and then over a cobalt thiomolybdate catalyst. The effluent from the second stage hydrogenation can be deemed a mixture of aromatics and saturated hydrocarbons and sufficiently free from olefins to be suitable for solvent extraction.

It should be recognized that there are overlaps in the boiling points of hydrocarbons of the $C_5$–$C_8$ range, so that a $C_6$ $C_7$ cut obtained economically by industrial distillation procedures usually contains measureable amounts of $C_5$ and $C_8$ hydrocarbons. Moreover, differences in feedstock and operating conditions both at the steam cracking step, and in the purification steps, can lead to variations in the composition of such hydrogenated $C_6$ $C_7$ dripolene. The weight percentage of benzene in such stream is generally within a range from about 35% to about 65% and the weight percentage of toluene is generally within a range from about 2% to about 35% and the unit ratio of benzene to toluene is generally within a range from about 5 to 25. The paraffin content, and particularly the branched paraffins, of the non-aromatic portion is high, with relatively low concentrations of cyclohexane, methyl cyclohexane, ethyl cyclopentane, and methyl cyclopentane, and related naphthenes, as compared with many virgin naphthas. However, the efficiency of an aromatics extraction step is significantly affected by the naphthene content of a feedstock. Such hydrogenated $C_6$ $C_7$ dripolene contains sufficient naphthenes to significantly affect the efficiency and operation conditions for the aromatics extraction operation.

In the control procedure, a hydrogenated $C_6$ $C_7$ dripolene is subjected to aromatics extraction to provide streams of benzene, toluene, and raffinate, each having an appropriate value. Financial analysis of the operation indicates that the value of the products would amount to a base figure corresponding to what has been commercial operation for several years, during which the raffinate has been directed to the pool for blending into gasoline.

CONTROL B

By following all of the procedure of Control A, but directing the raffinate from the aromatics extraction to supplement the feed to the reformer in the gasoline refinery, the value of the marketable products is increased measurably. Various combinations of extracting aromatics from dripolene and subjecting raffinate to reforming have been proposed, but their profitability has varied in response to the fluctuations in the relative prices of toluene, benzene, reformate, and suitable feedstock for a reformer. The raffinate from aromatics extraction is a less satisfactory component for reforming than a corresponding $C_6$ $C_7$ cut of virgin naphtha. Moreover reforming conditions are adjusted to optimize profits for the total available feedstocks, demand for specific ranges of octane rating of the reformate, etc, so that reforming conditions are often mismatched for such raffinate.

By a series of similar controls, it is established that prior art teachings relating to successive hydrogenative treatments of $C_6$ $C_7$ dripolene fractions fail to provide satisfactory methods for utilizing the dripolene.

EXAMPLE I

Kerosene is steam cracked as in Control A, and the two stages of hydrogenation are conducted.

Analysis of the $C_6$ $C_7$ hydrogenated dripolene showed the following composition:

|  | Weight % |
| --- | --- |
| Miscellaneous $C_6$ minus | 1.0 |
| Methyl cyclopentane | 6.8 |
| Cyclohexane | 1.9 |
| Benzene | 59.6 |
| Toluene | 21.7 |
| $C_7$ nonaromatic | 2.9 |
| Miscellaneous | 6.1 |

|  | Weight % |
| --- | --- |
|  | 100.0 |

Said $C_6$ $C_7$ hydrogenated dripolene was hydrogenatively aromatized at 951° F. at an hourly liquid space velocity of 3, at a pressure of 100 psig and at a hydrogen to hydrocarbon unit mol ratio of about 7 over a catalyst consisting of sorptive alumina matrix, about 1% chloride, and about 0.35% platinum during a run of about 92 hours to produce products as follows:

| $C_1$ $C_4$ hydrocarbons | 2.88 |
| --- | --- |
| Methyl Cyclo Pentane | 0.78 |
| other $C_6$ $C_7$ nonaromatics | 2.55 |
| Benzene | 63.40 |
| Toluene | 28.52 |
| Miscellaneous hydrocarbons | 1.87 |
|  | 100.00 |

Such data suggested that the hydrogenative aromatizing increased the aromatics content from about 81% to about 92%, whereby the subsequent step of aromatics extraction was more efficiently conducted. The fact that the concentration of naphthenes such as methyl cyclopentane was reduced particularly helped such efficiency of the aromatics extraction step. The partition coefficient for aromatics versus paraffins is more favorable than the partition coefficient for aromatics versus naphthenes.

EXAMPLE II

The same feedstock was hydrogenatively aromatized over the same catalyst at the same space rate as in Example I, but using the lower temperature of 900° F. instead of 950° F. and using a higher pressure of 150 psig instead of 100 psig. The product distribution data, on a no loss basis, were:

| $C_1$ $C_5$ hydrocarbons | 1.17 |
| --- | --- |
| Methyl Cyclo Pentane | 3.01 |
| Benzene | 63.31 |
| other $C_6$ $C_7$ nonaromatics | 5.26 |
| Toluene | 25.86 |
| Miscellaneous | 1.39 |
|  | 100.00 |

The conversion of cyclohexane and methyl cyclopentane to benzene was not as complete as in Example I, but the success in aromatizing a feedstock having an aromatics content as high as hydrogenated dripolene feedstock at such conditions was encouraging.

CONTROL C

The same feedstock employed in Example I was employed at the same temperature, catalyst, and pressure as Example I with an increased space rate as the only modification. The product distribution data when using an hourly liquid space rate of 7.3 instead of 3.0 were:

|  | Weight % |
| --- | --- |
| $C_5$ minus hydrocarbons | 2.31 |
| Methyl Cyclo Pentane | 3.61 |
| Benzene | 58.15 |
| other Non-aromatic $C_6$ $C_7$ | 5.16 |
| Toluene | 28.53 |

|  | Weight % |
|---|---|
| Miscellaneous | 2.24 |
|  | 100.00 |

Such data indicated that the extent of marginal aromatization at the 7.3 LHSV was inadequate. By a series of tests it is shown that the LHSV should not exceed about 5 but should be above 0.5 in accordance with the present invention.

By a similar series of tests it is established that the pressure must be maintained between 75 and 250 psig at a hydrogen to hydrocarbon ratio within a range from about 2 to 1 to about 10 to 1.

CONTROL D

The hydrogenated $C_6$ $C_7$ dripolene feedstock of Example I was subjected to hydrogenative aromatization at a LHSV of 3.6 (acceptable) at a hydrogen to hydrocarbon unit mol ratio of 7 (acceptable) over the catalyst (acceptable) of Example I, but the results were unsatisfactory because both the temperature, 800° F. and the pressure, 50 psig, were unacceptably low. Data relating to the product stream were:

|  | Weight % |
|---|---|
| $C_1$ $C_5$ Hydrocarbons | 2.69 |
| Methyl Cyclo Pentane | 6.06 |
| Cyclohexane | 0.86 |
| Benzene | 52.27 |
| $C_6$ $C_7$ non-aromatics | 5.22 |
| Toluene | 26.15 |
| Miscellaneous | 1.71 |

The extent of conversion of the cyclohexane and methylcyclopentane was only about 20% and thus too low to justify the process step. By a series of similar tests it is established that the temperature must be within a range from 850° F. to 1000° F. By a series of similar tests it is established that the platinum concentration must be within a range from 0.2% to 2%.

EXAMPLE III

A hydrogenated dripolene stream was analyzed and found to contain:

|  | Weight % |
|---|---|
| $C_4$ $C_5$ hydrocarbons | 19.08 |
| Methyl cyclopentane | 6.26 |
| Cyclohexane | 1.45 |
| Benzene | 47.21 |
| Non-aromatic $C_6$ $C_7$ hydrocarbons | 8.68 |
| Toluene | 16.52 |
| Miscellaneous | 0.87 |

The hydrogenated dripolene was hydrogenatively aromatized over a catalyst consisting of about 0.6% platinum, 1% chloride, and about 96% alumina, at a temperature of about 950° F. at a LHSV of 3.6 at 150 psig at a hydrogen to hydrocarbon unit mol ratio of 7 to prepare product stream data as shown:

|  | Weight % |
|---|---|
| $C_1$—$C_4$ | 3.80 |
| $C_5$ | 16.33 |
| Methylcyclopentane | 0.33 |
| Cyclohexane | 0.04 |
| Benzene | 52.89 |
| Non-aromatic $C_6$ $C_7$ | 5.66 |

|  | Weight % |
|---|---|
| Toluene | 19.36 |
| Miscellaneous | 1.29 |

Such data indicate that much of the cyclohexane and methyl cyclopentane were converted to benzene at the stated conditions.

By a series of tests it is established that the invention features a process in which a hydrocarbon is subjected to steam cracking to prepare unsaturated streams of $C_2$, $C_3$ and $C_4$ hydrocarbons, and to prepare a dripolene, and in which a hydrogenated hydrocarbon stream substantially free from olefins and cycloolefins is prepared from the dripolene said hydrogenated stream consisting predominantly of $C_6$ $C_7$ hydrocarbons, the improvement which consists of subjecting said hydrogenated $C_6$ $C_7$ hydrocarbon stream plus a hydrogen rich recycle stream providing from 2 to 10 mols of hydrogen per mol of hydrogenated $C_6$ $C_7$ hydrocarbon to a hydrogenative aromatizing zone containing a catalyst consisting predominantly of an activated alumina matrix, said catalyst containing at least 0.2 weight percent platinum but not more than 2 weight percent platinum, said catalyst having about 1 weight percent chloride, at a liquid hourly space velocity within a range from 0.5 to 5 at a pressure within the range from 75 psig to 250 psig at a temperature within the range from 850° F. to 1000° F. to produce an effluent, the liquid portion of which is subjected to aromatics extraction to produce significantly more benzene plus toluene than was present in the hydrogenated $C_6$ $C_7$ hydrocarbon stream subjected to said hydrogenative aromatizing step.

The invention claimed is:

1. In a process in which a hydrocarbon stream is subjected to steam cracking to prepare unsaturated streams of $C_2$, $C_3$, and $C_4$ hydrocarbons, and to prepare a dripolene containing benzene and toluene, and in which said dripolene is employed to prepare a $C_6$–$C_7$ hydrogenated hydrocarbon stream containing at least 35% by weight benzene and at least 2% by weight toluene the unit weight ratio of benzene to toluene being less than 25, said $C_6$–$C_7$ hydrogenated hydrocarbon stream being substantially free from olefins and cycloolefins, said $C_6$–$C_7$ hydrogenated stream consisting predominantly of $C_6$–$C_7$ hydrocarbons, the improvement which consists of:

subjecting a liquid hydrocarbon stream consisting only of said hydrogenated $C_6$–$C_7$ hydrocarbon stream to an aromatizing zone containing a catalyst consisting predominantly of an activated alumina matrix, said catalyst containing at least 0.2 weight % platinum but not more than 2 weight % platinum, said catalyst having about 1 weight % chloride, at a liquid hourly space velocity within a range from 0.5 to 5 at a pressure within the range from 75 psig to 250 psig at a temperature within the range from 850° F. to 1000° F. in the presence of a hydrogen rich recycle stream providing from 2 to 10 mols of hydrogen per mol of hydrocarbon in said liquid hydrocarbon stream to produce an effluent; and, subjecting the liquid portion of said effluent to aromatics extraction to recover significantly more benzene and toluene than was present in said hydrogenated $C_6$–$C_7$ hydrocarbon stream.

2. The process of claim 1 in which the said liquid hydrocarbon stream contains about 53% benzene and about 11% toluene and is subjected to said hydrogenative aromatizing zone at a liquid hourly space velocity of about 3 at a pressure of about 100 psig at a temperature of about 950° F.

* * * * *